(12) United States Patent
Kashiwagi et al.

(10) Patent No.: US 6,730,068 B2
(45) Date of Patent: May 4, 2004

(54) SANITARY NAPKIN

(75) Inventors: Masahiro Kashiwagi, Kagawa (JP); Wataru Yoshimasa, Kagawa (JP); Etsuko Tagami, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 105 days.

(21) Appl. No.: 10/188,736

(22) Filed: Jul. 3, 2002

(65) Prior Publication Data
US 2003/0023221 A1 Jan. 30, 2003

(30) Foreign Application Priority Data

Jul. 12, 2001 (JP) ........................................ 2001-212895

(51) Int. Cl.[7] ................................................ A61F 13/15
(52) U.S. Cl. .......................... 604/385.04; 604/385.01; 604/387
(58) Field of Search ................................ 604/358, 367, 604/379, 385.01, 385.03, 385.04, 386, 387

(56) References Cited

U.S. PATENT DOCUMENTS

| | | |
|---|---|---|
| 5,447,507 A | 9/1995 | Yamamoto |
| 5,730,738 A | 3/1998 | McFall et al. |
| 6,514,234 B2 * | 2/2003 | Shimizu et al. ........ 604/385.27 |

FOREIGN PATENT DOCUMENTS

| | | | |
|---|---|---|---|
| EP | 0 998 893 A2 | 5/2000 | |
| EP | 1 208 824 A2 | 5/2002 | |
| JP | 08-280735 | 10/1996 | ........... A61F/13/15 |
| WO | WO-96/23471 A1 | 8/1996 | |

* cited by examiner

*Primary Examiner*—Weilun Lo
*Assistant Examiner*—Michele Kidwell
(74) *Attorney, Agent, or Firm*—Darby & Darby

(57) ABSTRACT

Disclosed is a sanitary napkin having extensions. The sanitary napkin includes: a liquid-permeable topsheet disposed on one side of the sanitary napkin to cover a central region thereof; a backsheet; an absorbent layer disposed therebetween; and leakage preventing portions disposed on laterally opposed side portions of the topsheet and extending in a longitudinal direction of the sanitary napkin. Joints between the respective leakage preventing portions and the topsheet are formed to extend in the longitudinal direction. The extensions are portions of the sanitary napkin extending laterally outwardly beyond the joints. Each extension includes: a flexible region for facilitating folding thereof, which is spaced laterally outwardly apart from corresponding one of the joints: and a buffer region of a predetermined width between the flexible region and the corresponding joint. The compression energy of the buffer region in its thickness direction is in a range of 0.4 to 1.0 (N·m/m$^2$).

6 Claims, 3 Drawing Sheets

SANITARY NAPKIN

BACKGROUND OF THE INVENTION

1. Field of the Invention

The present invention relates to a sanitary napkin having laterally opposed leakage preventing portions on one side and extensions extending laterally outwardly beyond the leakage preventing portions. More particularly, the present invention relates to a sanitary napkin in which at least parts of the extensions can be folded back against a backsheet and fixed on an undergarment.

2. Description of the Related Art

It is required for sanitary napkins that a menstrual blood can be certainly absorbed by a liquid absorbent layer and never leaks out of the article while wearing. However, the conventional sanitary napkins are liable to deform when applied an external force due to a motion of a wearer. Therefore, if they are deformed in a state where the absorbency cannot be sufficiently exhibited, it is often the case that a menstrual blood will leak and clothing will be stained with the menstrual blood. Especially when the wearer walks, stands up, sits down, or takes exercise, the groin vigorously moves to easily cause a clearance between the worn article and the wearer's body. Therefore, the discharged liquid flows from the clearance, causing so-called lateral leakage, so that the clothing is stained with the discharged liquid.

Therefore, there has been made a proposal to prevent the lateral leakage in Japanese Unexamined Patent Publication No. H8-280735 (280735/1996) and so on, in which leakage preventing walls are formed on two sides of the article to extend in a longitudinal direction, and wing portions are provided to extend outwardly from the leakage preventing walls. Upon wearing, the wing portions are folded back against the outer side of the crotch portion of the undergarment and fixed on the outer side of the crotch portion through an adhesive layer. On two sides of the article, pocket-like recesses are formed between the leakage preventing walls and the absorbent body. Therefore, even if a menstrual blood is not absorbed by the absorbent body but flows along the topsheet, it can be dammed up by the recesses, thereby preventing the lateral leakage.

In this conventional sanitary napkin, since the article is fixed on the undergarment, the mobility in conjunction with the undergarment can be highly maintained.

In the conventional sanitary napkin, however, it is not always that the wing portions are folded back at the same positions. As a result, the sanitary napkin may possibly be attached to the crotch portion of the undergarment in a rightward or leftward offset position. Particularly when the wearer is in a hurry for changing the sanitary napkin for a new one in fear of stains on clothing, it is often the case that the sanitary napkin is worn without being attached to the undergarment in proper position.

If the sanitary napkin is attached to the crotch portion of the undergarment in a sidewardly offset position, when the wing portions are folded back against the outer side of the crotch portion of the undergarment, there is a strong probability that the root ends of the leakage preventing walls provided on the body-facing side of the sanitary napkin will be positioned at the folds near the root ends of the wing portions. If the root ends of the leakage preventing walls are positioned at the folds, the leakage preventing walls near the edges of the crotch portion of the undergarment are liable to deform, thereby deforming the pocket-like recesses.

In addition, if a sideward pressure is applied to the crotch portion of the undergarment due to compression by the thighs, such pressure directly acts on the root ends of the leakage preventing walls, which are positioned near the edges of the crotch portion of the undergarment. Therefore, the leakage preventing walls are liable to deform, causing a clearance between the leakage preventing walls and the wearer's skin. Moreover, the pocket-like recesses are also liable to deform, deteriorating the effect of preventing the liquid leakage.

SUMMARY OF THE INVENTION

The present invention has been worked out in view of the shortcoming in the prior art set forth above. It is therefore an object of the present invention to provide a sanitary napkin, which assures that when at least parts of extensions are folded back against an outer side of an undergarment, folds can be certainly spaced apart from root ends of leakage preventing portions and a sidewardly applied force can be relieved by a region between the fold and the leakage preventing portion, thereby preventing deformation of the leakage preventing portions and increasing the effect of preventing lateral leakage.

According to the invention, there is provided a sanitary napkin having extensions, at least parts of which are to be folded back and fixed on an undergarment in use, the sanitary napkin comprising:

a liquid-permeable topsheet disposed on one side of the sanitary napkin to cover at least a central region thereof;

a backsheet;

an absorbent layer disposed between the topsheet and the backsheet; and leakage preventing portions disposed on laterally opposed side portions of the topsheet and extending in a longitudinal direction of the sanitary napkin, joints between the respective leakage preventing portions and the topsheet being formed to extend in the longitudinal direction, the extensions being portions of the sanitary napkin extending laterally outwardly beyond the joints, wherein each extension includes: a flexible region for facilitating folding thereof, which is spaced laterally outwardly apart from corresponding one of the joints: and a buffer region of a predetermined width between the flexible region and the corresponding joint, a compression energy of the buffer region in a thickness direction thereof being in a range of 0.4 to 1.0 (N·m/m$^2$).

In the sanitary napkin, the buffer region is provided between the flexible region and the corresponding joint and the compression energy of the buffer region is set within the foregoing range. Therefore, a sidewardly applied pressure is relieved by the buffer region and hardly acts on the joint directly, thereby preventing deformation of the leakage preventing portion.

Preferably, a nonhydrophilic sheet is provided such that one portion thereof forms the leakage preventing portion and another portion thereof forms one surface of the extension, at least one intermediate sheet is disposed in the buffer region to be positioned between the backsheet and the extension surface-forming portion of the nonhydrophilic sheet, and the flexible region extends outwardly from an outwardly directed edge of the intermediate sheet. In the case where the buffer region is constructed to have at least three sheets, as set forth above, the compression energy of the buffer region can be easily set within the foregoing range.

Preferably, the intermediate sheet is not bonded to either overlying or underlying sheets. In this case, when a pressure is sidewardly applied to the buffer region, a clearance can be formed between the sheets, thereby increasing the ability of relieving the pressure.

It is also preferred that a portion of the leakage preventing portion-forming portion of the nonhydrophilic sheet is extended outwardly beyond the joint to form the intermediate sheet and/or that a portion of the topsheet is extended outwardly beyond the joint to form the intermediate sheet. In the case where the intermediate sheet is formed of the nonhydrophilic sheet or the topsheet, it is not required to separately provide the buffer region with another sheet for buffering, there by making the structure simple.

Preferably, the leakage preventing portion includes an elastic member for exhibiting an elastic contractive force in the longitudinal direction, and the leakage preventing portion is allowed to rise away from the topsheet while having the joint as a root end thereof. In this case, a liquid flowing along the topsheet can be certainly dammed up by the leakage preventing portion.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
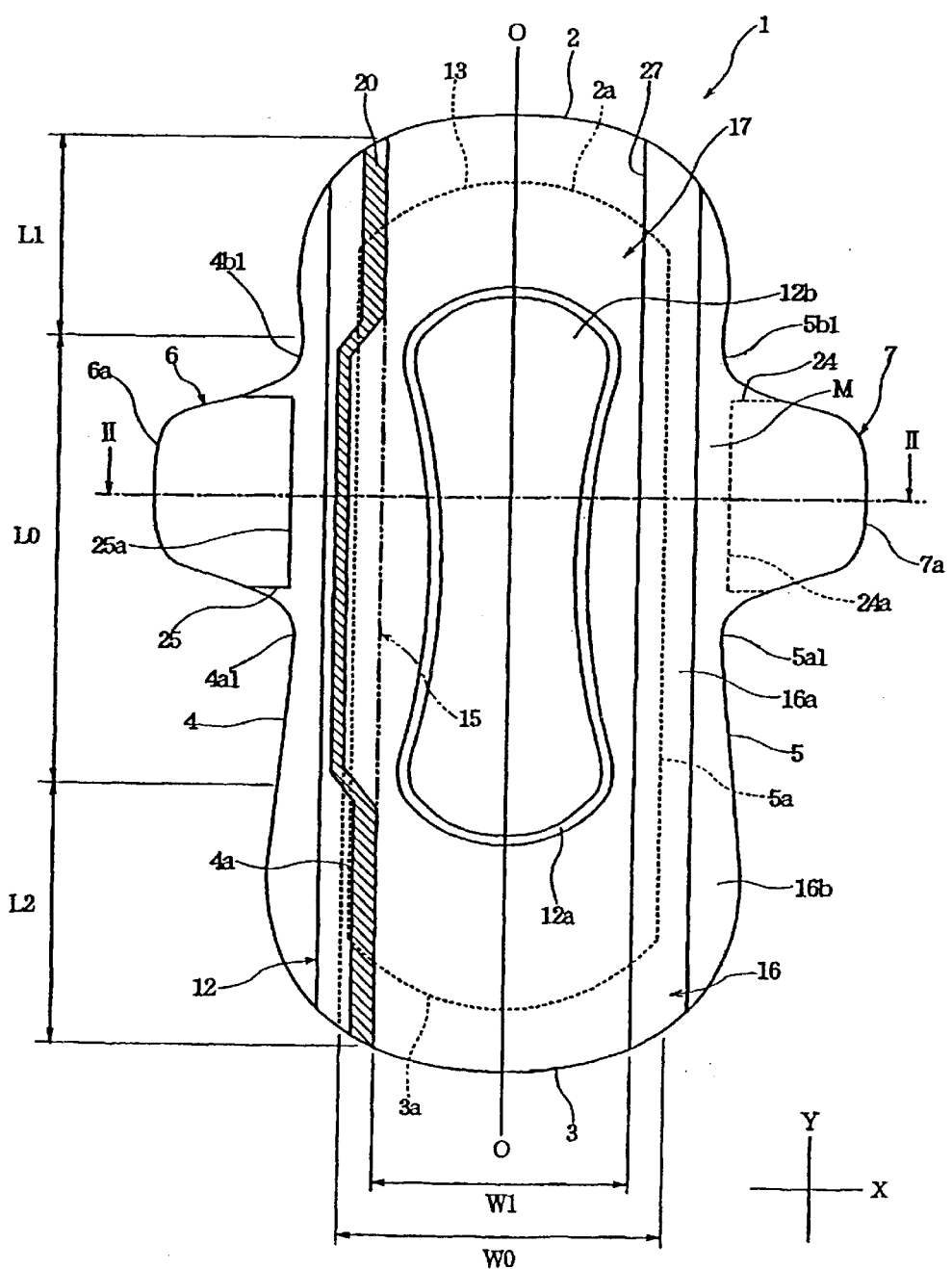
FIG. 1 is a top plan view showing a sanitary napkin according to one embodiment of the present invention, of which the left half with respect to a centerline O—O illustrates a state where a nonhydrophilic sheet is removed, and the right half illustrates a state where the nonhydrophilic sheet is attached.
Figure 2:
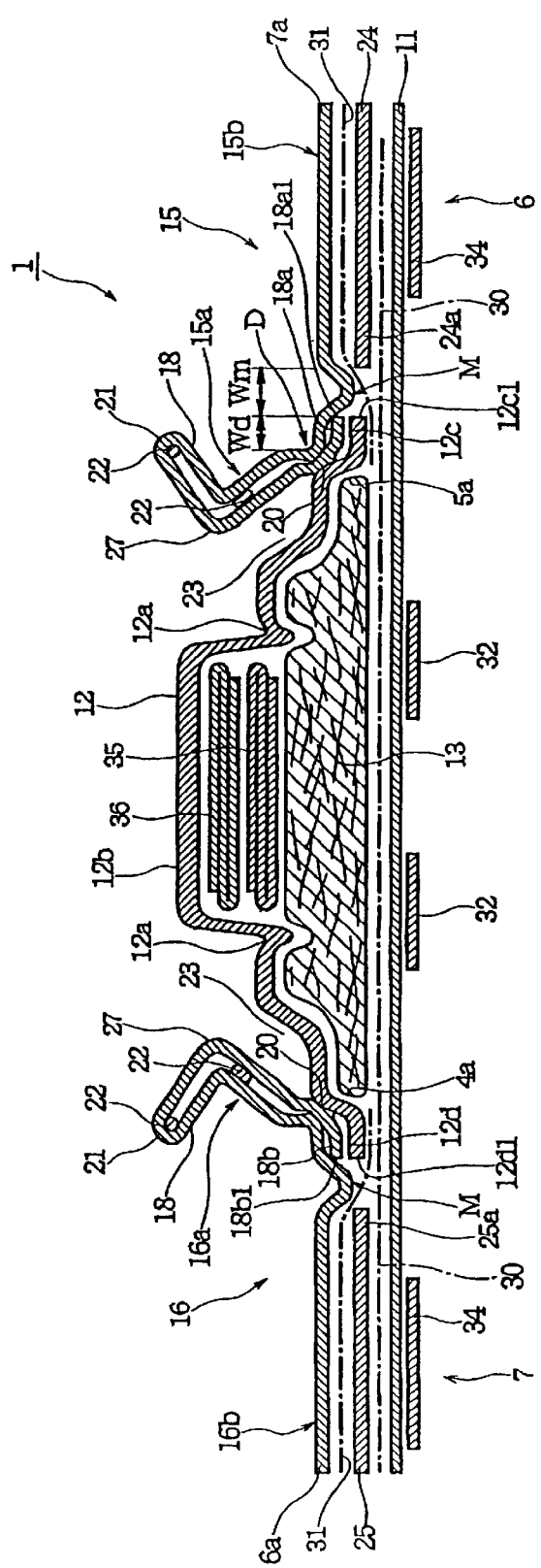
FIG. 2 is a sectional view taken along line II—II of FIG. 1.
Figure 3:
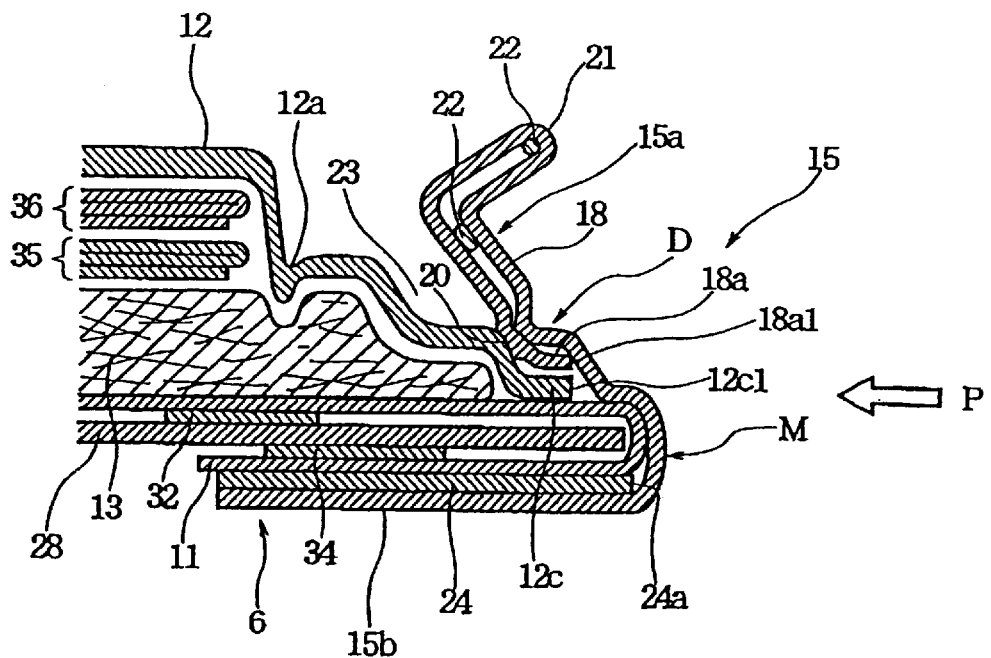
FIG. 3 is a sectional view of a part of the sanitary napkin which is attached to an undergarment.

FIG. 1 is a top plan view showing a sanitary napkin 1 according to one embodiment of the present invention, of which: the left half with respect to a centerline O—O illustrates a state where a nonhydrophilic sheet is removed; and the right half illustrates a state where the nonhydrophilic sheet is attached. FIG. 2 is a sectional view taken along line II—II of FIG. 1, and FIG. 3 is a sectional view of a part of the sanitary napkin which is attached to an undergarment.

The sanitary napkin 1 shown in FIGS. 1 and 2 is to be worn by a female during menstruation while being attached to an inner side of a crotch portion of an undergarment.

As seen from the top plan view of FIG. 1, the sanitary napkin 1 includes a main body portion having a generally arcuate front edge 2 and a rear edge 3 which is also arcuate. Left-hand and right-hand side edges 4 and 5 of the main body portion are slightly curved. The distance between the left-hand side edge 4 and the right-hand side edge 5, i.e., the width (dimension in the X-direction) of the main body portion of the sanitary napkin 1 may be constant or larger in the portion close to the rear edge 3 than in the portion close to the front edge 2.

The sanitary napkin 1 also includes wing portions 6 and 7 which extend laterally (in the X-direction) outwardly from the main body portion, in a position offset toward the front edge 2 from a laterally extending centerline of the sanitary napkin 1. The wing portions 6 and 7 have edges 6a and 7a continued to the side edges 4 and 5, respectively. In the embodiment shown, the wing portions 6 and 7 are part of extensions adapted to be folded back against an outer side of a crotch portion of an undergarment in use.

As shown in FIG. 2, the sanitary napkin 1 comprises a liquid-impermeable backsheet 11 and a liquid-permeable topsheet 12. The backsheet 11 is of an outline identical to that of the sanitary napkin 1 shown in FIG. 1, i.e., the backsheet 11 has the front edge 2, the rear edge 3, the left-hand side edge 4, the right-hand side edge 5, and the edges 6a and 7a of the wing portions 6 and 7.

The topsheet 12 is disposed within a range of a predetermined width containing the centerline O—O extending longitudinally of the sanitary napkin 1. Between the backsheet 11 and the topsheet 12, there is provided an absorbent layer 13.

The thickness of the absorbent layer 13 varies for different portions as shown in FIG. 2, and the outline of the absorbent layer 13 has a front edge 2a, a rear edge 3a, a left-hand side edge 4a and a right-hand side edge 5a, as shown in broken line in FIG. 1. The front edge 2a, rear edge 3a, left-hand side edge 4a and right-hand side edge 5a of the absorbent layer 13 are spaced inwardly apart from the front edge 2, rear edge 3, left-hand side edge 4 and right-hand side edge 5 of the sanitary napkin 1.

Between the absorbent layer 13 and the topsheet 12, there are disposed liquid-permeable sheets 35 and 36, which are respectively folded in three-ply structure and laid one upon the other. These liquid-permeable sheets 35 and 36 serve the function of rapidly drawing a menstrual blood given to the topsheet 12 and passing it to the absorbent layer 13. Along the periphery of the liquid-permeable sheets 35 and 36, the topsheet 12 and the absorbent layer 13 are heated under pressure to form a compressed groove 12a. In the compressed groove 12a, the density of the absorbent layer 13 is increased. The absorbent layer 13 is made thinner in its peripheral portion outside of the compressed groove 12a than in the central portion thereof. The portion having the liquid-permeable sheets 35 and 36 is raised from the compressed groove 12a to form a raised portion 12b. This raised portion 12b comes into close contact with a private part of a wearer, thereby certainly introducing the menstrual blood into the absorbent layer 13.

The lower surface of the absorbent layer 13 is bonded to the backsheet 11 through a hot-melt adhesive 30. On the other hand, the upper surface of the absorbent layer 13 and the upper surface of the liquid-permeable sheets 35, 36 are bonded to the topsheet 12 through a hot-melt adhesive (not shown), which is applied in a zigzag or spiral pattern so as not to inhibit the permeation of liquid.

On the wearer facing side of the sanitary napkin 1, the regions from positions laterally spaced apart from the centerline O—O to the side edges 4 and 5 of the main body portion and the edges 6a and 7a of the wing portions 6 and 7 are referred to as nonhydrophilic regions 15 and 16. Between the nonhydrophilic regions 15 and 16, there is provided a liquid-receiving region 17 in which the topsheet 12 is exposed.

In the nonhydrophilic regions 15 and 16, there are provided leakage preventing portions 15a and 16a extending substantially parallel to the longitudinal direction and extensions 15b and 16b extending laterally outwardly from the leakage preventing portions 15a and 16a. The wing portions 6 and 7 respectively include parts of the extensions 15b and 16b. The leakage preventing portions 15a and 16a and the extensions 15b and 16b are comprised of nonhydrophilic sheets 18.

In the respective leakage preventing portions 15a and 16a, each nonhydrophilic sheet 18 is folded back upon itself at the top 21, and the nonhydrophilic sheets 18 thus folded in two-ply structure are joined to the topsheet 12 at the root ends of the leakage preventing portions 15a and 16a to thereby form joints 20. Accordingly, the respective leakage preventing portions 15a and 16a are formed of a portion of the nonhydrophilic sheet 18 between the joint 20 and the top 21; and the respective extensions 15b and 16b are formed of another portion of the nonhydrophilic sheet 18 continuously extending from the joint 20 to the side edge 4 or 5 of the main body portion and the edge 6a or 7a of the wing portion 6 or 7.

Inside of the leakage preventing portions 15a and 16a, a plurality of elastic members 22 extending in the longitudinal direction are bonded. These elastic members 22 are bonded to the nonhydrophilic sheets 18 while being stretched, so that an elastic contractive force acts on the leakage preventing portions 15a and 16a along the longitudinal direction. In the front and rear regions of the sanitary napkin 1, on the other hand, the portions of the nonhydrophilic sheets 18 forming the leakage preventing portions 15a and 16a are folded in a flat state and fixed on the surface of the topsheet 12 as a whole. Therefore, when the sanitary napkin 1 is in a free state, the sanitary napkin 1 is curved due to the elastic contractive force, so that the leakage preventing portions 15a and 16a are raised with their tops 21 moved away from the surface of the sanitary napkin 1, in the intermediate region between the front and rear portions of the sanitary napkin 1. The leakage preventing portions 15a and 16a thus raised have longitudinally extending fold lines 27 and 27 at the midpoints of their heights, so that the leakage preventing portions 15a and 16a are given the cross-sectional shape of substantially V (rotated 90 degrees).

Between the topsheet 12 and the inner wall surfaces of the leakage preventing portions 15a and 16a at positions below the fold lines 27 and 27, then, there are formed pocket-like recesses 23 and 23. These recesses 23 can dam up a menstrual blood, which could not be absorbed by the absorbent layer 13 and has laterally flowed down the topsheet 12.

Here, as seen from the left half of FIG. 1, the distance between one joint 20 at the root end of the leakage preventing portion 15a and the other joint 20 at the root end of the leakage preventing portion 16a is indicated at W0 in the intermediate region of a length L0, and indicated at W1 in the front region of a length L1 and the rear region of a length L2. The distance W0 is larger than the distance W1. That is, the liquid-receiving region 17 is slightly wider in the intermediate region.

At least in the intermediate region of the length L0, as shown in FIG. 2, laterally opposed end portions of the topsheet 12 extend laterally outwardly beyond the joints 20 and 20, functioning as intermediate sheets 12c and 12d. In addition, end portions of the nonhydrophilic sheets 18 adjacent to the portions forming the inner wall surfaces of the leakage preventing portions 15a and 16a also extend laterally outwardly beyond the joints 20 and 20, functioning as intermediate sheets 18a and 18b.

Here, the intermediate sheets 12c and 12d formed of the end portions of the topsheet 12 are bonded onto the surface of the backsheet 11 through hot-melt adhesives 30 and 31; but the intermediate sheets 18a and 18b formed of the end portions of the nonhydrophilic sheets 18 are not bonded to either the overlying portions of the nonhydrophilic sheets 18 and 18 or the underlying intermediate sheets 12c and 12d.

In the wing portions 6 and 7 of the extensions 15b and 16b, on the other hand, reinforcing sheets 24 and 25 are sandwiched between the backsheet 11 and the nonhydrophilic sheets 18. The lower surfaces of the reinforcing sheets 24 and 25 are bonded to the backsheet 11 through the hot-melt adhesive 30, and the upper surfaces of the reinforcing sheets 24 and 25 are bonded to the nonhydrophilic sheets 18 through the hot-melt adhesives 31.

The reinforcing sheets 24 and 25 are similar in shape to the wing portions 6 and 7. Inwardly directed edges 24a and 25a of the reinforcing sheets 24 and 25 are outwardly spaced apart from the joints 20 and 20 at the root ends of the leakage preventing portions 15a and 16a, and the edges 24a and 25a are in parallel relationship with the joints 20 and 20.

In FIG. 1, the boundaries between the main body portion of the sanitary napkin 1 and the wing portions 6 and 7 are indicated by 4a1–4b1 and 5a1–5b1, respectively. The edge 25a of the reinforcing sheet 25 and the edge 24a of the reinforcing sheet 24 are spaced outwardly apart from the boundaries 4a1–4b1 and 5a1–5b1, respectively.

Then, the region inside of the edge 24a of the reinforcing sheet 24 and outside of the edges 12c1 and 18a1 of the intermediate sheets 12c and 18a has a low stiffness and is referred to as a flexible region M. In this flexible region M, the backsheet 11 and the nonhydrophilic sheet 18 are stacked and bonded to each other through the hot-melt adhesives 30 and 31. Similarly, the region inside of the edge 25a of the reinforcing sheet 25 and outside of the edges 12d1 and 18b1 of the intermediate sheets 12d and 18b is another flexible region M, in which the backsheet 11 and the nonhydrophilic sheet 18 are stacked and bonded to each other through the hot-melt adhesives 30 and 31.

In order to permit the wing portions 6 and 7 to be folded back against an outer side of a crotch portion of an undergarment 28 while positioning the intermediate sheets 12c, 12d and 18a, 18b on an inner side of the crotch portion, as shown in FIG. 3, the width Wm of the flexible region M is required to be larger than the thickness of the undergarment 28, preferably at least 4 mm. Here, although there is no special reason to establish the upper limit of the width Wm, the upper limit will be about 15 mm according to the size of commonly used sanitary napkins.

In addition, the dimension Wd, which is larger one of the distance from the joint 20 to the edge 12c1 of the intermediate sheet 12c and the distance from the joint 20 to the edge 18a1 of the intermediate sheets 18a, i.e., which is larger one of the dimension over which the intermediate sheet 12c is laterally outwardly extended from the joint 20 and the dimension over which the intermediate sheet 18a is laterally outwardly extended from the joint 20, is preferably at least 2 mm, more preferably at least 3 mm. With the dimension Wd being thus set, when worn as shown in FIG. 3, the joint 20 can be positioned inwardly apart from the edge of the crotch portion of the undergarment 28. Therefore, even when a force P is applied from side of the crotch portion, the force P hardly acts on the joint 20 and the leakage preventing portion 15a directly. In the embodiment shown, therefore, the region of the width Wd is referred to as a buffer region D. It should be also noted that although there is no special reason to establish the upper limit of the width Wd, the upper limit will be about 5 mm, 8 mm, or 10 mm at the maximum, according to the size of commonly used sanitary napkins.

Of course, the opposite side having the reinforcing sheet 25 is also provided with another buffer region D having the same width Wd.

Here, in order that the buffer region D of the width Wd can provide a sufficient buffering effect on a sideward force in the worn state of FIG. 3, the energy of compression of the buffer region D, as measured using an Automatic Compression Tester "KES FB3-A" manufactured by KATO TECH, Japan, is preferably 0.4 to 1.0 (N·m/m$^2$). Below the foregoing limit, the buffer region D is too soft to provide sufficient buffering ability. In excess of the foregoing limit, on the other hand, the sheets forming the buffer region D are thick, and therefore, the wearer may possibly feel an unpleasantness.

In the extensions 15b, 16b, if it is assumed that the Gurley stiffness of the flexible regions M, M is 1, the Gurley stiffness of the buffer regions D, D and the Gurley stiffness of the wing portions 6, 7 respectively having the reinforcing sheets 24, 25 are preferably equal to or more than 2.5 and equal to or less than 9. Here, the buffer region D means the region where the intermediate sheet 12c or 12d and the intermediate sheet 18a or 18b are provided, as set forth above. Below the foregoing range, since the flexible regions cannot be clearly distinguished from other regions in folding back the wing portions 6 and 7, there is a possibility of causing fold near the joints 20 or in positions where the reinforcing sheets 24 and 25 are provided. In excess of the foregoing range, since the stiffness of the regions near the flexible regions M is excessively increased, there is a possibility of giving a stiff feeling to a wearer.

Here, the Gurley stiffness of the flexible region M is measured as follows. First, a laminate of sheets identical to the backsheet 11 and the nonhydrophilic sheet 18 forming the flexible region M is prepared, and the laminate is cut into a test sample having a size of 51 mm (corresponding to the length of the flexible region M)×12.7 mm (corresponding to the width of the flexible region M). Then, the longitudinal end of the test sample is held in a chuck of a Gurley Stiffness Tester (manufactured by YASUDA SEIKI, Japan), and then the stiffness (mN) is measured by taking the reading on a pendulum as the chuck is swung at a constant speed. Similarly, laminates of sheets identical to those forming the buffer region D and the wing portions 6 and 7 are respectively prepared, and cut into test samples having the same size. The Gurley stiffnesses of these test samples are measured in the same manner. Combinations of sheets may be selected so that the Gurley stiffness ratio of the flexible region M to the buffer region D and the wiping portions 6 and 7 is in a range of from 1:2.5 to 1:9. It should be noted that this Gurley Stiffness Test is carried out based on JIS-L1018.

As shown in FIG. 2, in the wing portions 6 and 7, pressure sensitive adhesive layers 34 and 34 for fixing to the undergarment are provided on the lower surface of the backsheet 11. In the main body portion of the sanitary napkin 1, on the other hand, strip-shaped pressure sensitive adhesive layers 32 and 32 are provided on the lower surface of the backsheet 11. Before use, release sheets are adhered to the surfaces of the pressure sensitive adhesive layers 34 and 34 and the surfaces of the pressure sensitive adhesive layers 32 and 32.

Hereinbelow, preferred materials for forming the sanitary napkin 1 will be described.

The backsheet 11 is a liquid-impermeable sheet, as exemplified by a resin film formed of PE (polyethylene), PP (polypropylene), PET (polyethylene terephthalate), EVA (ethylene-vinyl acetate copolymer), or a combination of two or more thereof. The resin film may be finely apertured to provide moisture permeability by adding filler or the like and then elongating it. In an alternative, a laminate of resin and paper, a laminate of nonwoven fabric and resin film or the like may be employed.

The topsheet 12 is a liquid-permeable sheet, as exemplified by a resin film formed of PE, PP, PET, EVA, or a combination of two or more thereof, which is formed with a large number of apertures having a size sufficient to allow a liquid to pass through it, or a fibrous nonwoven fabric in which composite fibers containing PE, PP, PET, etc. are entangled or bonded using heated air, pressure, water flow or the like.

For the absorbent layer 13, a mixture of crushed pulp and SAP (superabsorbent polymer) wrapped in a liquid-permeable paper or cellulose sheet, cellulose fibers processed with a binder into a sheet form, fluff pulp, air-laid pulp, open-cell type hydrophilic foam, thin paper, spunlaced nonwoven fabric comprising hydrophilic fibers, meltblown nonwoven fabric treated to be hydrophilic, absorbent paper, cotton linter pulp, or combinations thereof may be employed. However, any other materials may be employed as long as suitable for use as the absorbent layer.

The liquid-permeable sheets 35 and 36 are formed of a bulky nonwoven fabric superior in absorbency of liquid, for instance.

The nonhydrophilic sheet 18 is preferably formed of a flexible material which can prevent permeation and penetration of liquid. For example, employed is a through-air bonded nonwoven fabric comprising PP fibers or bicomponent fibers of PE/PP, PE/PET, PP/EVA or the like having a fineness of 1.1 to 6.7 dtex. If the fineness is below 1.1 dtex, the capillary attraction is increased to disadvantageously attract a discharged liquid and absorb a discharged liquid once absorbed by the absorbent layer 13. If the fineness is in excess of 6.7 dtex, the stiffness of the fibers is increased to deteriorate a feel upon wearing.

The through-air bonded nonwoven fabric employed as the nonhydrophilic sheet 18 preferably has a basis weight of 10 to 40 g/m$^2$. If the basis weight is less than 10 g/m$^2$, a discharged liquid once absorbed by the absorbent layer 13 is liable to flow out of it when a pressure is applied. If the basis weight is more than 40 g/m$^2$, a feel upon wearing is deteriorated. As an alternative to the through-air bonded nonwoven fabric, a spunbonded nonwoven fabric produced by continuously spinning fibers may also be employed. The through-air bonded or spunbonded nonwoven fabric may be laminated with PE resin. Such laminating may be performed over the entire surface of the nonwoven fabric or partially. In the case where the laminating is performed over the entire surface of the nonwoven fabric, it is preferred that the laminated film is made as thin as possible, desirably, equal to or less than 10 μm, so as not to deteriorate a feel upon wearing due to the increased stiffness of the sheet. In the case where the laminating is performed partially on the nonwoven fabric, on the other hand, the area ratio of the laminated film to the nonwoven fabric is preferably equal to or less than 50% so as not to deteriorate a feel upon wearing due to the increased stiffness of the sheet.

As another embodiment of the nonhydrophilic sheet 18, a resin film formed of a resin such as PE, PP or EVA may be used. In this case, it is preferred that the resin film has a basis weight of 10 to 35 g/m$^2$.

As the elastic members 22 used in the leakage preventing portions 15a and 16a, an olefin film or yarn, a urethane elastic yarn or foam, or a natural rubber in the form of filament or ribbon may be employed alone or in combination.

For the reinforcing sheets 24 and 25, a through-air bonded nonwoven fabric, a spunbonded nonwoven fabric or a resin film similar to those of the nonhydrophilic sheet 18 can be employed. In addition, these reinforcing sheets 24 and 25 are preferably nonhydrophilic. Alternatively, the reinforcing sheets 24 and 25 may be formed of paper. In order to provide some stiffness, it is preferred that paper to be used as the reinforcing sheets 24 and 25 is not creped. It is also possible that two or more sheets of the foregoing nonwoven fabrics, resin film and paper are combined for the reinforcing sheets 24 and 25.

As shown in FIG. 3, when the sanitary napkin 1 is attached to the crotch portion of the undergarment 28, the pressure sensitive adhesive layers 32 and 32 provided in the main body portion are first pressed against the inner side of the crotch portion of the undergarment 28 for fixing the main body portion. Thereafter, the wing portions 6 and 7 are folded at the flexible regions M and M, turned back upon the outer side of the crotch portion of the undergarment 28., and then pressed against the outer side of the crotch portion of the undergarment 28 through the pressure sensitive adhesive layers 34 for fixing.

Here, when the flexible regions M and M having a width of at least 4 mm serve as folds along which the wing portions 6 and 7 are to be folded back, the wing portions 6 and 7 can be folded back and fixed on the outer side of the crotch portion of the undergarment 28 such that the edges 24a and 25a of the reinforcing sheets 24 and 25 substantially match the left-hand and right-hand side edges of the crotch portion of the undergarment 28. On the other hand, the buffer regions D and D having the intermediate sheets 12c, 12d and the intermediate sheets 18a, 18b can be positioned near the left-hand and right-hand side edges of the crotch portion, on the inner side of the undergarment 28.

Here, in the case where the Gurley stiffness of the buffer regions D and D having the intermediate sheets 12c, 12d and the intermediate sheets 18a, 18b and the Gurley stiffness of the wing portions 6 and 7 having the reinforcing sheets 24 and 25 are 2.5 to or 9 times the Gurley stiffness of the flexible regions M, the wing portions 6 and 7 can be readily folded at the flexible regions M and M.

In addition, since the edge 24a of the reinforcing sheet 24 and the edge 25a of the reinforcing sheet 25 are positioned outside of the boundaries 4a1–4b1 and 5a1–5b1, the inside portions of the extensions 15b and 16b other than the wing portions 6 and 7 are effectively prevented from being folded back against the outer side of the crotch portion of the undergarment 28.

Moreover, when the buffer regions D and D having the intermediate sheets 12c, 12d and the intermediate sheets 18a, 18b are positioned on the inner side of the crotch portion of the undergarment 28, the joints 20 and 20 are also positioned inside of the left-hand and right-hand side edges of the crotch portion of the undergarment 28. Therefore, the leakage preventing portions 15a and 16a can be certainly raised toward the wearer's skin from the joints 20 and 20 to closely contact the skin. If the buffer regions D and D were not provided, the joints 20 and 20, after folding the wing portions 6 and 7, might be positioned at the folds near the left-hand and right-hand side edges of the crotch portion of the undergarment 28. In this case, the leakage preventing portions 15a and 16a are liable to fall down outwardly, thereby making it difficult to dam up a liquid with the pocket-like recesses 23. In the shown embodiment, however, since the buffer regions D and D having a width of at least 2 mm are provided outside of the joints 20 and 20, the leakage preventing portions 15a and 16a can be certainly raised toward the wearer from the inner side of the crotch portion of the undergarment 28.

Moreover, even when the force P is applied to the side portions of the sanitary napkin 1 due to pressure from the thigh of the wearer (from the direction P), such force P is relieved by the buffer regions D and D having the intermediate sheets 12c, 12d and the intermediate sheets 18a, 18b, so that the force P is prevented from directly acting on the joints 20 and 20 being the root ends of the leakage preventing portions 15a and 16a. Therefore, the leakage preventing portions 15a and 16a are hardly deformed and are maintained in the raised position. As a result, the pocket-like recesses 23 and 23 can be certainly maintained between the topsheet 12 and the inner wall surfaces of the leakage preventing portions 15a and 16a, so that a menstrual liquid laterally flowing along the topsheet 12 can be dammed up by the recesses 23 and 23.

Especially, if the compression energy of the buffer regions D and D is set within a range of 0.4 to 1.0 (N·m/m$^2$), as set forth above, the force P sidewardly applied from the thigh in the worn state of FIG. 3 hardly acts on the leakage preventing portions 15a and 16a directly, thereby preventing deformation of the leakage preventing portions 15a and 16a.

Still moreover, since the nonhydrophilic sheets 18 are bonded to the nonhydrophilic backsheet 11 in the flexible regions M and M, even if a menstrual blood flowing along the topsheet 12 goes beyond the joints 20 and 20, it can be dammed up in the flexible regions M and M, thereby preventing the wearer's skin from being stained with such menstrual blood. Furthermore, since the menstrual blood permeating through the flexible regions M and M can be dammed up between the backsheet 11 and the nonhydrophilic sheet 18 by the edges 24a and 25a of the nonhydrophilic reinforcing sheets 24 and 25, it never permeates through the wing portions 6 and 7. Therefore, the menstrual blood can be prevented from reaching the exterior surface of the undergarment 28.

Figure 4:
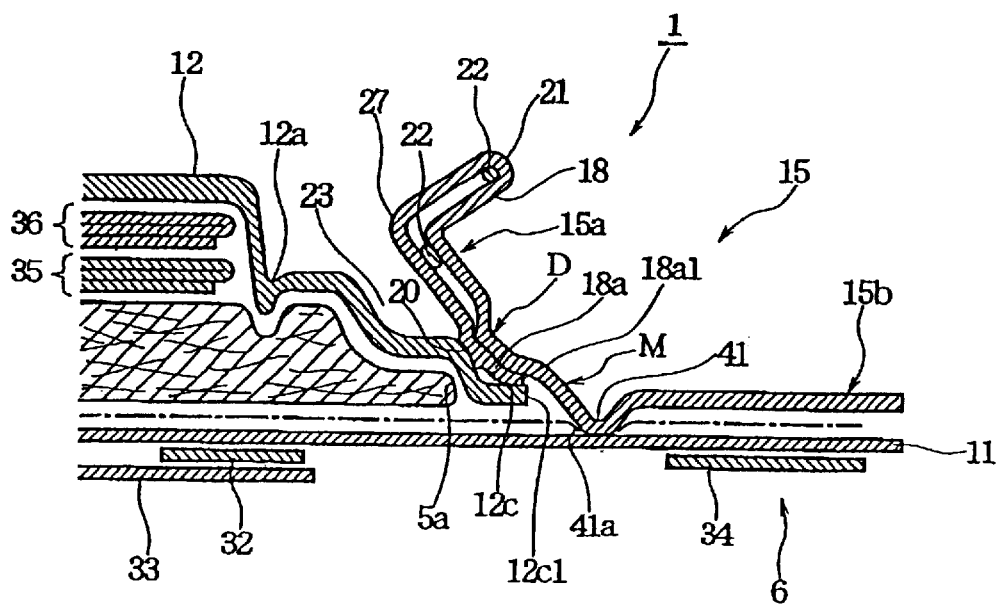
FIG. 4 is a sectional view showing a half of a sanitary napkin according to another embodiment of the present invention.

FIG. 4 is a sectional view showing a half of a sanitary napkin according to another embodiment of the present invention. Here, the detailed description of the portions having the same constructions as those of the first embodiment will be omitted by designating them by the common reference numerals.

In the embodiment shown in FIG. 4, the backsheet 11 and the nonhydrophilic sheet 18 are heat-fused together under pressure to form a continuously or intermittently embossed portion 41 in parallel relationship with the joint 20, in the respective extensions 15b and 16b. On the other hand, the intermediate sheets 12c and 18a are provided in the same manner as in the first embodiment. The intermediate sheet 18a is not bonded to either the overlying sheet or the underlying sheet.

Therefore, a difference in stiffness is caused between the embossed portion 41 and the remaining portions, so that the flexible region M is formed between the inner edge 41a of the embossed portion 41 and the edges 12c1 and 18a1 of the intermediate sheets 12c and 18a, and the region having the intermediate sheets 12c and 18a functions as the buffer region D.

In this case, too, it is preferred that the compression energy of the buffer region D is set within a range of 0.4 to 1.0 (N·m/m$^2$).

In the foregoing embodiments, each buffer region D is formed by extending the topsheet 12 and the nonhydrophilic sheet 18 beyond the joint 20. However, it is also possible that another intermediate sheet separate from the topsheet 12 and the nonhydrophilic sheet 18 is provided, to thereby form the flexible region M outside of the outwardly directed edge of the intermediate sheet thus provided.

EXAMPLES

Examples according to the present invention will be described hereinbelow in comparison with Comparative Examples, but the present invention should not be construed as limited thereto.

In the disclosure, the compression energy of the buffer region D is expressed by the value measured using the Automatic Compression Tester "KES FB3-A" manufactured by KATO TECH, Japan.

First, a sheet laminate having the same construction as that of the buffer region D of the sanitary napkin was prepared as a test sample, and put on the Automatic Compression Tester. Then, an initial pressure T0 of 49 Pa (0.5 g/cm$^2$) is applied to the test sample with the circular pressure plate having an area of 2 cm$^2$. Then, the compression pressure is increased linearly at a compression rate of 50 mm/second from the initial pressure T0 to the maximum compression pressure Pm of 4,900 Pa (50 g/cm$^2$). Tm represents the thickness of the test sample when the maximum compression pressure Pm is applied thereto. At this time, the compression energy WC per unit area (m$^2$) of the test sample is expressed by a value of the definite integral between Tm and T0, i.e., WC=∫P·dT (P indicates pressure; T indicates thickness).

For Comparative Examples 1 to 6 and Example 1, at first, test samples having a length 100 mm and a width of 100 mm were prepares as follows, and their compression energies were measured using the Automatic Compression Tester. In each sample, a polyethylene film having a basis weight of 23.5 g/m$^2$ was used as the backsheet 11, and a spunbonded nonwoven fabric formed of PE/PP bicomponent synthetic fibers to have a basis weight of 22 g/m$^2$ was used as the nonhydrophilic sheet 18.

Comparative Example 1

No intermediate sheet was provided between the backsheet 11 and the nonhydrophilic sheet 18.

Comparative Example 2

Non-creped paper having a basis weight of 30 g/m$^2$ was provided as the intermediate sheet between the backsheet 11 and the nonhydrophilic sheet 18.

Comparative Example 3

One sheet of spunbonded nonwoven fabric formed of PE/PP bicomponent synthetic fibers to have a basis weight of 22 g/m$^2$ was provided as the intermediate sheet between the backsheet 11 and the nonhydrophilic sheet 18.

Comparative Example 4

One sheet of through-air bonded nonwoven fabric formed of PE/PET bicomponent synthetic fibers to have a basis weight of 25 g/m$^2$ was provided as the intermediate sheet between the backsheet 11 and the nonhydrophilic sheet 18.

Comparative Example 5

One sheet of spunbonded nonwoven fabric formed of PE/PET bicomponent synthetic fibers to have a basis weight of 22 g/m$^2$ and two sheets of through-air bonded nonwoven fabric formed of PE/PET bicomponent synthetic fibers to have a basis weight of 25 g/m$^2$ were provided as the intermediate sheets between the backsheet 11 and the nonhydrophilic sheet 18.

Comparative Example 6

One sheet of polyethylene film having a large number of apertures for liquid permeation and having a basis weight of 27 g/m$^2$ was provided as the intermediate sheet between the backsheet 11 and the nonhydrophilic sheet 18.

Example 1

One sheet of spunbonded nonwoven fabric formed of PE/PET bicomponent synthetic fibers to have a basis weight of 22 g/m$^2$ and one sheet of through-air bonded nonwoven fabric formed of PE/PET bicomponent synthetic fibers to have a basis weight of 25 g/m$^2$ were provided as the intermediate sheets between the backsheet 11 and the nonhydrophilic sheet 18. This test sample was prepared in accordance with the structure of the buffer region D of the sanitary napkin shown in FIG. 2.

For Comparative Examples 1 to 6 and Example 1, moreover, sanitary napkins having their buffer regions D constructed similar to the respective test samples, were prepared. The sanitary napkin was attached to the crotch portion of the undergarment, as shown in FIG. 3. Then, how the leakage preventing portion was deformed upon applying a pressure to the side edge of the crotch portion was observed. In addition, the sanitary napkins were worn by monitors, letting them evaluate the feel upon wearing.

The evaluation of the deformation of the leakage preventing portions and the feel upon wearing are shown in Table 1. When the leakage preventing portion was badly deformed, it was indicated by X in Table 1.

TABLE 1

| | Sheet between Leakage preventing portion and Backsheet | Compression energy (N · m/m²) | Effect on Shape of Leakage preventing portion | Feel upon Wearing |
|---|---|---|---|---|
| Com. Ex. 1 | — | 0.127 | x | good |
| Com. Ex. 2 | 30 g/m² non-creped paper | 0.176 | x | good |
| Com. Ex. 3 | one sheet of 22 g/m² PE/PP spunbonded nonwoven | 0.213 | x | good |
| Com. Ex. 4 | one sheet of 25 g/m² PE/PET through-air bonded nonwoven | 0.354 | x | good |
| Com. Ex. 5 | one sheet of 22 g/m² PE/PP spunbonded nonwoven + two sheets of 25 g/m² PE/PET through-air bonded nonwoven | 1.270 | good | thick |
| Com. Ex. 6 | one sheet of 27 g/m² PE apertured film | 0.364 | x | good |
| Ex. 1 | one sheet of 22 g/m² PE/PP spunbonded nonwoven + one sheet of 25 g/m² PE/PET through-air bonded nonwoven | 0.513 | good | good |

In Example 1, since the compression energy of the buffer region was in the range of 0.4 to 1.0 (N·m/m²), the leakage preventing portions were hardly deformed, while providing a good feel upon wearing. In Comparative Examples 1–4 and 6, on the other hand, since the compression energy of the buffer region was less than 0.4 (N·m/m²), the leakage preventing portions were badly deformed. In Comparative Example 5, since the compression energy was more than 1.0 (N·m/m²), the buffer regions outside the leakage preventing portions was felt thick upon wearing.

As has been described above, the sanitary napkin according to the present invention can be readily positioned on the inner side of the crotch portion of the undergarment. Moreover, even if a force is applied from side of the crotch portion, the leakage preventing portions are hardly deformed. Therefore, the effect of preventing leakage due to the leakage preventing portions can be constantly obtained.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary napkin having extensions, at least parts of which are to be folded back and fixed on an undergarment in use, the sanitary napkin comprising:
   a liquid-permeable topsheet disposed on one side of the sanitary napkin to cover at least a central region thereof;
   a backsheet;
   an absorbent layer disposed between the topsheet and the backsheet; and
   leakage preventing portions disposed on laterally opposed side portions of the topsheet and extending in a longitudinal direction of the sanitary napkin, joints between the respective leakage preventing portions and the topsheet being formed to extend in the longitudinal direction, the extensions being portions of the sanitary napkin extending laterally outwardly beyond the joints, wherein
   each extension includes: a flexible region for facilitating folding thereof, which is spaced laterally outwardly apart from corresponding one of the joints: and a buffer region of a predetermined width between the flexible region and the corresponding joint, a compression energy of the buffer region in a thickness direction thereof being in a range of 0.4 to 1.0 (N·m/m²).

2. The sanitary napkin as set forth in claim 1, wherein a nonhydrophilic sheet is provided such that one portion thereof forms the leakage preventing portion and another portion thereof forms one surface of the extension, at least one intermediate sheet is disposed in the buffer region to be positioned between the backsheet and the extension surface-forming portion of the nonhydrophilic sheet, and the flexible region extends outwardly from an outwardly directed edge of the intermediate sheet.

3. The sanitary napkin as set forth in claim 2, wherein the intermediate sheet is not bonded to either overlying or underlying sheets.

4. The sanitary napkin as set forth in claim 2, wherein a portion of the leakage preventing portion-forming portion of the nonhydrophilic sheet is extended outwardly beyond the joint to form the intermediate sheet.

5. The sanitary napkin as set forth in claim 2, wherein a portion of the topsheet is extended outwardly beyond the joint to form the intermediate sheet.

6. The sanitary napkin as set forth in claim 1, wherein the leakage preventing portion includes an elastic member for exhibiting an elastic contractive force in the longitudinal direction, and the leakage preventing portion is allowed to rise away from the topsheet while having the joint as a root end thereof.

* * * * *